(12) United States Patent
Hendi et al.

(10) Patent No.: US 9,291,618 B2
(45) Date of Patent: Mar. 22, 2016

(54) POROUS NOBLE METAL OXIDE NANOPARTICLES, METHOD FOR PREPARING THE SAME AND THEIR USE

(71) Applicant: King Saud University, Riyadh (SA)

(72) Inventors: Awatif Ahmed Hendi, Riyadh (SA); Manal A. Awad, Riyadh (SA); Nada E. Eisa, Riyadh (SA); Khaled M. Ortashi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/468,485

(22) Filed: Aug. 26, 2014

(65) Prior Publication Data

US 2015/0219633 A1 Aug. 6, 2015

(30) Foreign Application Priority Data

Feb. 5, 2014 (EP) .................................... 14153962

(51) Int. Cl.
| | |
|---|---|
| *G01N 33/52* | (2006.01) |
| *G01N 33/50* | (2006.01) |
| *G01N 33/00* | (2006.01) |
| *C01G 7/00* | (2006.01) |
| *C07G 5/00* | (2006.01) |
| *B82Y 15/00* | (2011.01) |
| *B82Y 40/00* | (2011.01) |
| *C01G 5/00* | (2006.01) |

(52) U.S. Cl.
CPC *G01N 33/52* (2013.01); *C01G 7/00* (2013.01); *B82Y 15/00* (2013.01); *B82Y 40/00* (2013.01); *C01G 5/00* (2013.01); *C01P 2004/03* (2013.01); *C01P 2004/04* (2013.01); *C01P 2004/16* (2013.01); *C01P 2004/32* (2013.01); *C01P 2004/53* (2013.01); *C01P 2004/64* (2013.01); *C01P 2006/12* (2013.01); *C01P 2006/14* (2013.01); *C01P 2006/40* (2013.01); *C01P 2006/90* (2013.01); *Y10S 977/773* (2013.01); *Y10S 977/896* (2013.01); *Y10S 977/957* (2013.01); *Y10T 428/2982* (2015.01); *Y10T 436/173845* (2015.01)

(58) Field of Classification Search
CPC ..... G01N 31/22; G01N 31/221; G01N 31/00; G01N 33/50; G01N 33/52; G01N 33/5308; Y10T 436/17; Y10T 436/173845; B22F 9/24; B22F 9/18; B22F 9/16; B22F 9/00
USPC .................. 436/111, 106; 424/618, 600, 649
See application file for complete search history.

(56) References Cited

U.S. PATENT DOCUMENTS

2007/0218555 A1* 9/2007 Paknikar ................ A01N 59/16
435/410
2011/0003085 A1 1/2011 Hugener-Campbell et al.

FOREIGN PATENT DOCUMENTS

| EP | 2671846 | 12/2013 | |
|---|---|---|---|
| EP | 2 878 401 A1 * | 6/2015 | ................ B22F 9/24 |
| WO | 2010120964 | 10/2010 | |

OTHER PUBLICATIONS

STN Seach Report, by STIC at the United States Patent and Trademark Office, generated on Jul. 10, 2015, pp. 1-138.*

* cited by examiner

*Primary Examiner* — Christine T Mui
(74) *Attorney, Agent, or Firm* — Renner, Otto, Boisselle & Sklar, LLP (57) ABSTRACT

The present invention discloses a method for preparing porous noble metal oxide nanoparticles, comprising the following steps: a) preparing an *Olea Europaea* fruit extract; b) preparing an *Acacia Nilotica* extract; c) mixing the *Olea Europaea* fruit extract and the *Acacia Nilotica* extract for preparing a mixed extract; d) providing an aqueous solution containing a noble metal compound dissolved therein; e) mixing the mixed extract obtained in step c) and the aqueous solution of step d); f) dropping a solution of sodium chloride to be mixture of step b); g) drying the mixture, in air or by vacuum, and h) calcining at a temperature between 100 to 900° C., to get the porous noble metal oxide nanoparticles; porous noble metal oxide nanoparticles obtained thereby and their use.

16 Claims, 7 Drawing Sheets

POROUS NOBLE METAL OXIDE NANOPARTICLES, METHOD FOR PREPARING THE SAME AND THEIR USE

CROSS-REFERENCE TO RELATED APPLICATION

The present application is based on and claims priority under 35 U.S.C. §119(a) to European Application No. 14153962.7, filed on Feb. 5, 2014, the entirety of which is hereby incorporated herein by reference.

TECHNICAL FIELD

The present invention relates to porous noble metal oxide nanoparticles, a method for preparing the same, and their use.

BACKGROUND

Nanoparticles are of great scientific interest as they can be utilized in many industrial or medical applications. Nanoparticles are typically sized between 1 to 100 nm.

In particular, gold nanoparticles have been intensively studied as they are versatile materials having interesting chemical, electronic and optical properties for a broad range of different applications. The properties and applications of gold nanoparticles, especially of porous gold oxide nanoparticles strongly depend on their respective shape and size.

Possible applications of gold nanoparticles and porous gold oxide nanoparticles lie, for example, in the fields of nanoelectronics, imaging, sensing, catalysis, optics, environmental industry, energy development and biomedicine. Due to the low metal oxidation potential of gold nanoparticles, they can be used in medical diagnostic tests, such as labeling, X-ray contrasting, immunestrain and phago kinetic tracking studies, in targeted drug delivery techniques, as well as in medical therapies.

Silver nanoparticles and porous silver oxide nanoparticles have various and important applications. Historically, silver has been known to have a disinfecting effect and has been found in applications ranging from traditional medicines to culinary items. It has been reported that silver nanoparticles (AgNPs) and silver oxide nanoparticles (AgONPs) are non-toxic to humans and most effective against bacteria, virus and other eukaryotic micro-organism at low concentrations and without any side effects. Moreover, several salts of silver and their derivatives are commercially manufactured as antimicrobial agents. In small concentrations, silver is safe for human cells, but lethal for microorganisms. Antimicrobial capability of AgNPs and AgONPs allows them to be suitably employed in numerous household products such as textiles, as well as disinfection in water treatment, food storage containers, home appliances and in medical devices. The most important application of silver, AgNPs and AgONPs is in medical industry such as topical ointments to prevent infection against burn and open wounds.

Several methods for producing porous noble metal oxide nanoparticles have been developed which utilize harsh conditions. Wet methods often require the application of aggressive reducing agents, for example sodium borhydride, capping agents and may additionally need organic solvents such as toluene or chloroform. Furthermore, often toxic compounds must be employed or are produced during the synthesis of porous noble metal oxide nanoparticles. Although known methods may produce successfully porous noble metal oxide nanoparticles, energy preparation consumption and pollution effects are relatively high, as well as material and environmental costs. Even the availability of some materials, in particular of biomaterials, as for example plant materials, may be a problem. In consequence, there remains a need for more cost-effective and environmentally benign alternative methods for producing porous noble metal oxide nanoparticles with improved properties on a large scale. Main criteria for a green chemistry synthesis of stabilized nanoparticles are the choice of eco-friendly and non-hazardous solvents, reducing agents and capping agents, especially for porous noble metal oxide nanoparticles which shall be utilized in medical treatment.

Biological synthesis of nanoparticles by plant extracts is at present under exploitation as some researchers worked on it and tested them for antimicrobial activities.

Chemical reduction methods are widely used for synthesizing AgONPs because of their readiness to generate AgONPs under gentle conditions and their ability to synthesize AgONPs on a large scale.

U.S. Pat. No. 5,540,834 discloses methods for the preparation of porous inorganic particles, preferably $ZrO_2$ particles, that have a porosity of about 5-60%. The method involves the step of combining an aqueous sol comprising a colloidal dispersion of inorganic particles with a polymerizable organic material, polymerizing the organic material and forming aggregates over the polymer and inorganic colloidal particles, collecting the aggregates and pretreating them in a generally oxygen-free atmosphere, pyrolyzing the pretreated aggregates at temperature of less than 550° C. in an oxygen atmosphere and sintering the substantially polymer-free particles.

U.S. Pat. No. 5,182,016 relates to polymer-coated carbon-clad inorganic oxide particles, preferably $ZrO_2$, which are useful in sorbent applications. The carbon-clad $ZrO_2$ particles are preferably prepared by a low pressure chemical vapor deposition (CVD) method.

U.S. Pat. No. 7,276,224 B2 discloses methods of producing nanoporous particles by spray pyrolysis of a precursor composition including a reactive precursor salt and a nonreactive matrix salt, wherein the matrix salt is used as a templating medium. By this method nanoporous aluminum oxide particles which have a pore size of at least about 2 nm and no greater than 25 nm are provided.

X. L. Zhai et al., *Chin. Chem. Lett.*, 15, 1342-1344 (2004) reports on porous carrier MgO which was aggregated by nanoparticles that have been firstly prepared by using a normal technology route. The MgO was rod-shaped and had large surface area.

Z. Lu et al., *Int. J. Electrochem. Sci.*, 8, 3564-3571 (2013) describes Ag—Zn alloy that are dealloyed in 0.1M $H_2SO_4$ at a low temperature to fabricate nanoporous silver. The dealloying process involves the dissolution of the less noble element and a formation/coarsening of the nanoporous structure by surface diffusion of the more noble element. The formation of nanoporous structure is a process of selective dissolution of zinc atoms and diffusion of gold atoms at alloy/electrolyte interfaces.

For the last two decades extensive work has been done to develop new drugs from natural products because of the resistance of microorganisms to the existing drugs. Nature has been an important source of products currently being used in medical practice.

There are various strategies for using gold nanoparticles as a drug delivery vehicle, including systems based on covalent binding or drug encapsulation. Furthermore, it has been reported that antibiotics often disturb the bacterial flora of digestive tract which may develop multiple drug-resistant isolates, hence noble ways of formulating biocide materials is an upcoming field of attraction. For this reason, there is a need for the use of an agent which does not generate resistance and presents a good bactericidal property. Gold nanoparticles have a great bactericidal effect on several ranges of microorganisms.

A number of synthetic methods have been employed for the synthesis of silver-based nanoparticles involving physical, chemical and biochemical techniques. However, these chemical synthesis methods employ toxic chemicals in the synthesis route which may have adverse effect in the medical applications and hazard to environment.

SUMMARY

Preparation of porous noble metal oxide nanoparticles by green synthesis approach has advantages over physical and chemical approaches as it is environmental friendly, cost effective and the most significant advantage is that conditions of high temperature, pressure, energy and toxic chemicals are not required in the synthesis protocol.

It is an object of the present invention to provide a method for preparing porous noble metal oxide nanoparticles using green chemistry synthetic techniques which overcomes the drawbacks of the prior art. Especially, a method shall be provided which allows the use of non-toxic, abundant eco-friendly bioavailable material and which enables saving energy and costs. It is a further object to provide porous noble metal oxide nanoparticles which show improved medical properties and can be utilized in industrial and medical applications.

The first object is achieved by a method for preparing porous noble metal oxide nanoparticles, comprising the following steps:

a) preparing an *Olea Europaea* fruit extract
b) preparing an *Acacia Nilotica* extract
c) mixing the *Olea Europaea* fruit extract and the *Acacia Nilotica* extract for preparing a mixed extract
d) providing an aqueous solution containing a noble metal compound dissolved therein
e) mixing the mixed extract obtained in step c) and the aqueous solution of step d)
f) dropping a solution of sodium chloride to the mixture of step e)
g) drying the mixture, preferably in air or by vacuum, and
h) calcining at a temperature between 100 to 900° C., to get the porous noble metal oxide nanoparticles.

By the term "nanoparticle" is meant a microscopic particle with at least one dimension less than 100 nm.

Preferably, the mixed extract obtained in step c) contains oleic acids and/or pentacyclic triterpenoids as effective group.

Within the present application, the term "effective group" is to be understood, that the effective group containing compound of the mixed extract plays a main role, for example, as reducing and/or stabilizing agent for the inventive porous noble metal oxide nanoparticles. One or more different effective group(s) may be alone or together responsible for these effects.

It is preferred that the porous noble metal oxide nanoparticles are more preferably calcined at a temperature between 300 to 750° C.

It is preferred that the preparation of the *Olea Europaea* fruit extract is performed by adding deionized or distilled water to *Olea Europaea* fruit, preferably grinding it and then filtering the extract.

In a preferred embodiment, the preparation of the *Acacia Nilotica* extract is performed by adding deionized or distilled water to *Acacia Nilotica*, preferably soaking it and then filtering the extract.

Alternatively, the term "extract" of the present invention means an extract obtained from bioavailable plant and/or fruit materials. The extract may be obtained by using standard extraction techniques, like a reparatory funnel, a soxhlet apparatus and so on. Further, the extraction may comprise one or more different extraction steps in which the same or different extraction techniques may be used.

More preferably, the *Olea Europaea* fruit extract and the *Acacia Nilotica* extract are mixed in a range of weight mixing ratios from 5:1 to 1:5, preferably in ratios of 7:3, 3:1, 1:1 or 1:3.

It is also preferred that the mixing in step e) includes stirring at 25° C., putting the mixture into a shaker for 30 min at 145 rpm, shaking the mixture in a water bath at 125 rpm at 60° C. or leaving the mixture for about 3 months at room temperature.

More preferably, the mixing of step e) is preferably at room temperature.

According to the present invention, any mixing technique utilized in the art may be used.

Even preferred, the noble metal is selected from Au or Ag.

It is further preferred that the porous gold oxide nanoparticles shall be prepared by utilizing an inorganic acid containing Chloroauric Acid ($HAuCl_4$). When porous silver oxide nanoparticles shall be prepared, a solution of silver nitrate may be utilized and provided in step d).

Most preferably, the aqueous solution provided in step d) also comprises a surfactant, preferably cetyl trimethyl ammonium bromide (CTAB).

The second object is achived by porous noble metal oxide nanoparticles prepared by the inventive method wherein the particle size is within a range of 10-100 nm, preferably of 20-60 nm, more preferably is 40 nm.

It is further preferred that the porous noble metal oxide nanoparticles are substantially spherical or rod.

Even preferred, the porous noble metal oxide nanoparticles have a porous surface morphology.

In a further embodiment, the porous noble metal oxide nanoparticles are substantially monodispersed.

More preferably, the porous noble metal oxide nanoparticles are colloidal.

Even preferred, the porous noble metal oxide nanoparticles have a surface area of 0.05-150 $m^2/g$.

It is further preferred, that the porous noble metal oxide nanoparticles have a pore volume of 0.0001-0.7 $cm^3/g$.

Specific surface area, pore volume and average pore diameter were measured with TriStar II 3020 V1.03 (V1.03), Micromeritics, USA. Specific surface area of the samples was measured by adsorption of nitrogen gas at 150° C. and applying the Brunauer-Emmett-Teller (BET) calculation. Prior to adsorption, the samples were degassed automatic. Pore size distributions were derived from desorption isotherms at P/Po of 0.3 using the Barrett-Joyner-Halenda (BJH) method.

More preferably, the porous noble metal oxide nanoparticles show electrical conductivity.

A further object is achieved by the use of the inventive porous noble metal oxide nanoparticles in a catalytic, electronic, imaging, sensing, photonic, energy, optical, environmental, biotechnical or medical application.

More preferably, the porous noble metal oxide nanoparticles are preferably used in an automated sequential injection method for chemiluminescence determination of tramadol hydrochloride.

It was also found that the inventive porous noble metal oxide nanoparticles can be used in textile fabrication, in food storage containers, as antibacterial agent, in nanoelectronics, as biosensors, as biomedical tools, in sustainable energy development, in bioremediation of radioactive wastes, as functional electrical coating, in the synthesis of enzyme electrodes and particularly in medicine, such as for delivery of antigen for vaccination, gene delivery for treatment or prevention of genetic disorder, and drug delivery, in waste water treatment etc.

Surprisingly, it was found that the inventive method provides the possibility to synthesize porous noble metal oxide nanoparticles in an easy, energy saving and cost-efficient way from non-toxic, abundant natural materials and medical plants. In addition, the synthesis method of the invention is accomplished in a short time and is suitable for large scale preparation. Moreover, it was found that the inventive method allows faster nanoparticle growth, the possibility to achieve a variety of particle shapes and a better control of particle size distribution, compared to the prior art (US 2010/0055199A1). The inventive porous noble metal oxide nanoparticles may have several applications, such as antibacterial and cancer treatment, catalyst in chemical reactions, electrical batteries, in spectrally selective coatings for absorption of solar energy, as optical elements, in pharmaceutical components, chemical sensing, biosensing or in food and water storage.

The addition of sodium chloride (NaCl) shields the surface charge of the noble metal oxide nanoparticles and leads to a concomitant decrease in inter particle distance and eventually in particle aggregation. Solutions of porous AuONPs can be utilized as electrolyte solutions.

Nanoporous gold, already synthesized in the form of nanoparticles, possesses a much higher surface-to-volume ratio than bulk nanoporous gold films and gold nanoparticles. These nanoporous gold nanoparticles are expected to broaden the range of applications for both, gold nanoparticles and nanoporous gold, due to their two-level nanostructures, which consists of porosity of around 10 nm and the respective particle size of nanoparticles.

This invention focusses especially on a new method for synthesis of porous gold oxide nanorods and nanospheres. The preferred presence of surfactant molecules on the surface of the porous gold oxide nanorods and nanospheres strongly influences their reactivity and stability. The preparation of AuO nanorods and nanospheres according to the invention has advantages over physical and chemical approaches as it is eco-friendly, economical, clean and doesn't involve the use of any toxic chemical, as well as simple application and storage at room temperature and high stability. Porous gold oxide nanoparticles may be particularly utilized in applications such as gas storage, actuation, catalysis and sensing.

BRIEF DESCRIPTION OF THE DRAWINGS

The invention is now further illustrated by the accompanying figures and detailed description from which further features and advantages may be taken. It is to be noted that the following explanations are presented for the purpose of illustration and description only; they are not intended to be exhaustive or to limit the invention to the precise form disclosed.

DETAILED DESCRIPTION

Example 1

Porous gold oxide nanoparticles were synthesized by bioreduction of $AuCl_4^-$ ions. 10 g *Olea Europaea* fruit was washed carefully and was added to 10 ml deionized water. Then it was grinded, filtered and the extract was kept until it was used. 10 g *Acacia Nilotica* was added to 10 ml deionized water, soaked all the night, filtered and then the extract was kept until it was used. Equal volumes of the *Olea Europaea* fruit extract and *Acacia Nilotica* extract were mixed to prepare a mixed extract which preferably contains oleic acids and/or pentacyclic triterpenoids. 5 ml of the mixed extract was added to 50 ml of an aqueous solution of 0.25 mole/ml $HAuCl_4$ and 0.08 mole/L Cetyl trimethylammonium bromide (CTAB). The mixture has been stirred for about 10 minutes at 350° C. until an orange colored solution was obtained. When adding the organic extract the color changed, from orange transparent to colorless. These color change indicated the formation of the gold oxide nanoparticles. Afterward, 3 drops of sodium chloride were added and the mixture was dried in air. Additionally calcination of the porous gold oxide nanoparticles occurred at 400, 500, 600 or 700° C. for 4 hours.

A separation process for the extracts of *Olea Europaea* fruit extract and *Acacia Nilotica* extract was carried out by using a reparatory funnel and separated fractions were tested by TLC. It was clearly found that effective groups or preparing the nanoparticles comprise oleic acids and/or pentacyclic triterpenoids. These effective groups are actually responsible and play main role as reducing and stabilizing agent for the rapid formation of nanorods with high monodispersity.

The surface area was measured by BET method. The results are shown in Table 1.

TABLE 1

The relationship between the calcination temperatures, the surface area, pore volume and pore size of porous gold oxide nanoparticles.

| | Calcination Temperatures | | | |
| --- | --- | --- | --- | --- |
| | 400° C. | 500° C. | 600° C. | 700° C. |
| Surface Area m$^2$/g | 0.0766 | 0.179 | 1.8708 | 146.706 |
| Pore Volume cm$^3$/g | 0.000303 | 0.002181 | 0.007490 | 0.603574 |
| Pore Size nm | 22.3257 | 59.6814 | 21.4183 | 17.0949 |

Figure 1:
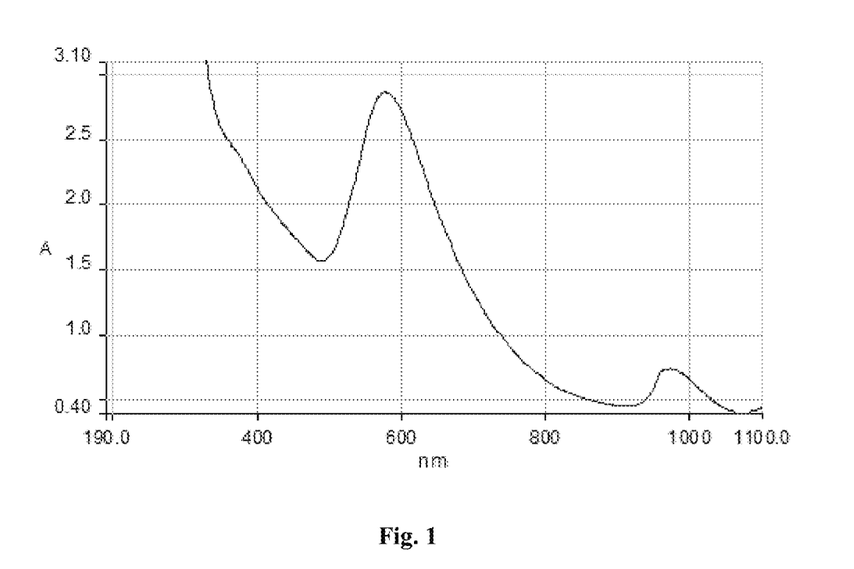
FIG. 1 shows a graph of UV-Vis spectrum of porous gold oxide nanoparticles synthesized by the inventive method chemistry synthetic techniques according to example 1.
Figure 2:
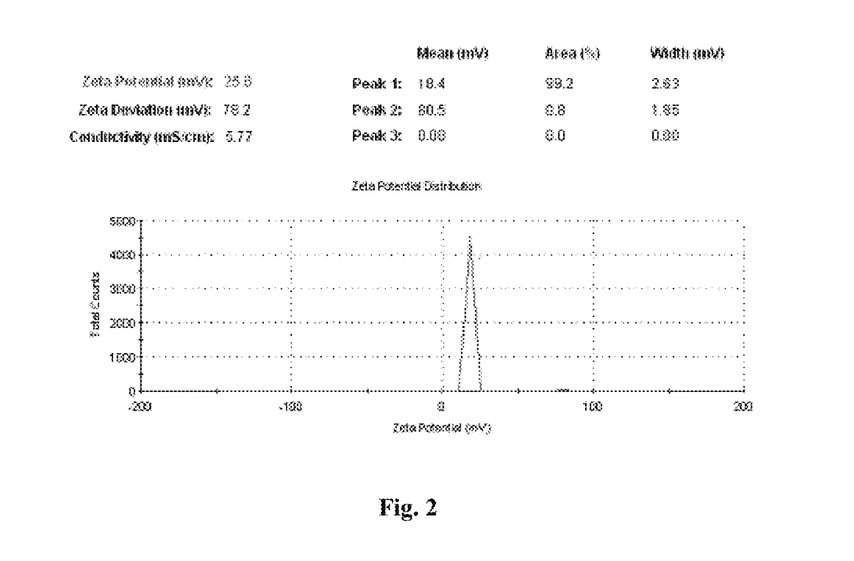
FIG. 2 shows a graph of Zeta sizer for measuring the average particle size of the porous gold oxide nanoparticles prepared according to the invention.
Figure 3:
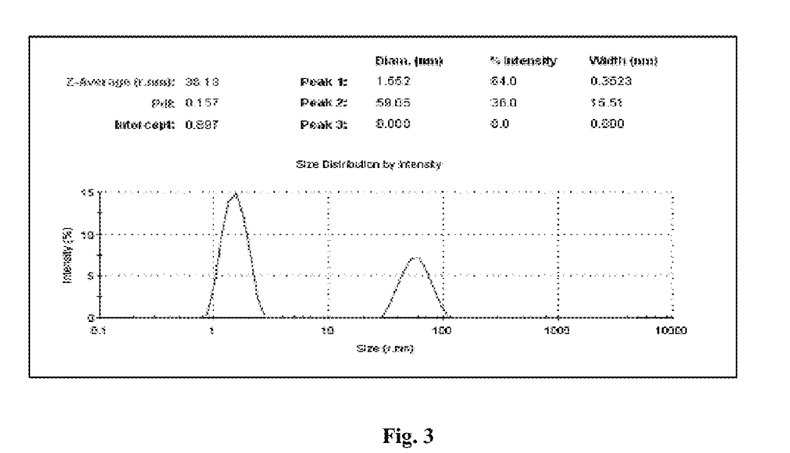
FIG. 3 shows a graph of particle size distribution of porous AuONPs synthesized by the inventive method.
Figure 4A:
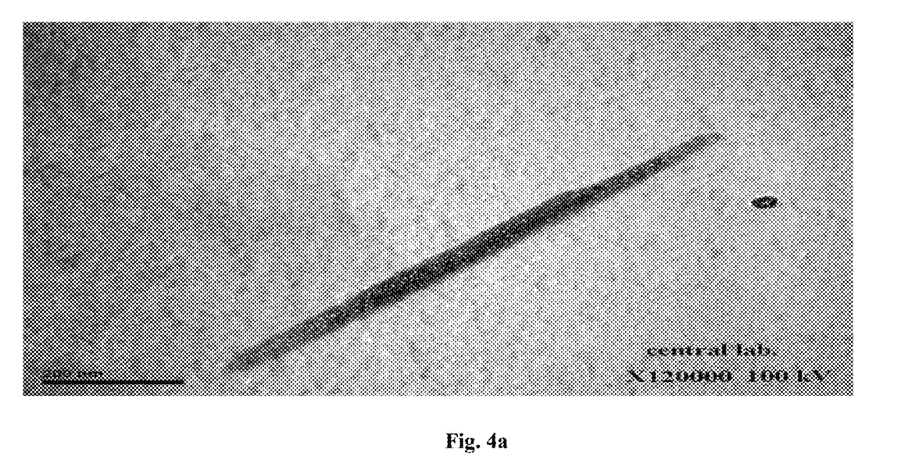
FIGS. 4a, 4b, 4c, 4d, 4e and 4f show a graph of transmission electron microscopy (TEM) image of porous gold oxide nanoparticles synthesized by the inventive method (100 KV) with different shapes and magnifications.
Figure 4B:
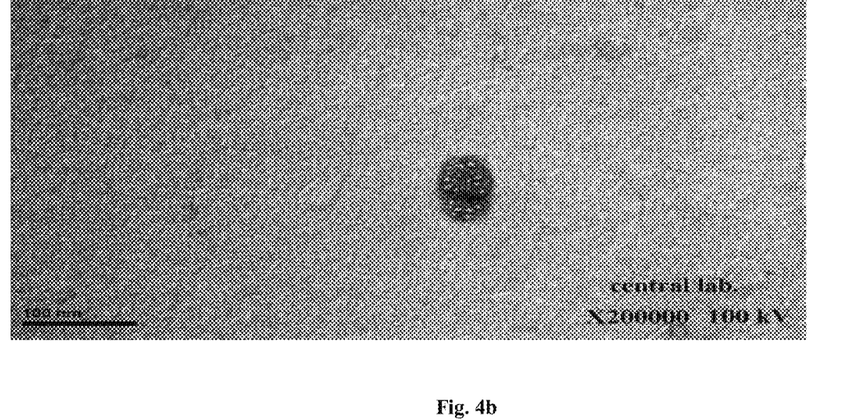
Figure 4C:
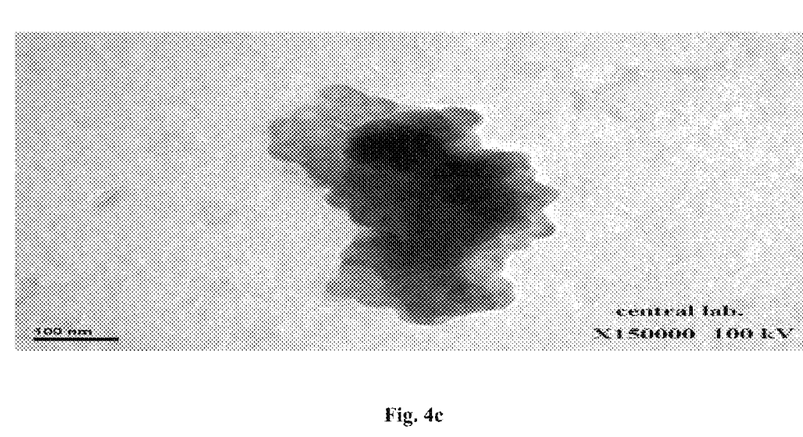
Figure 4D:
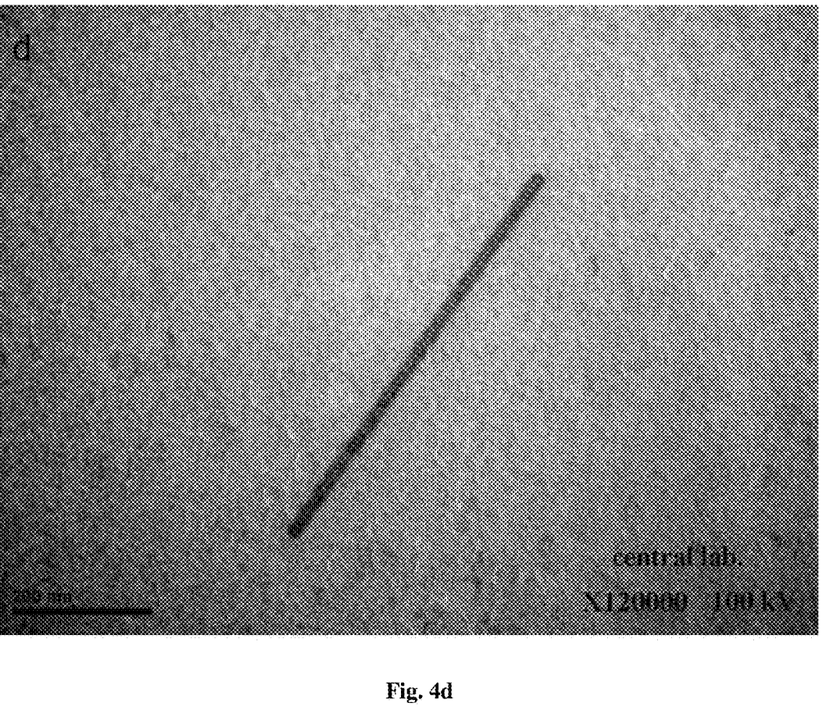
Figure 4E:
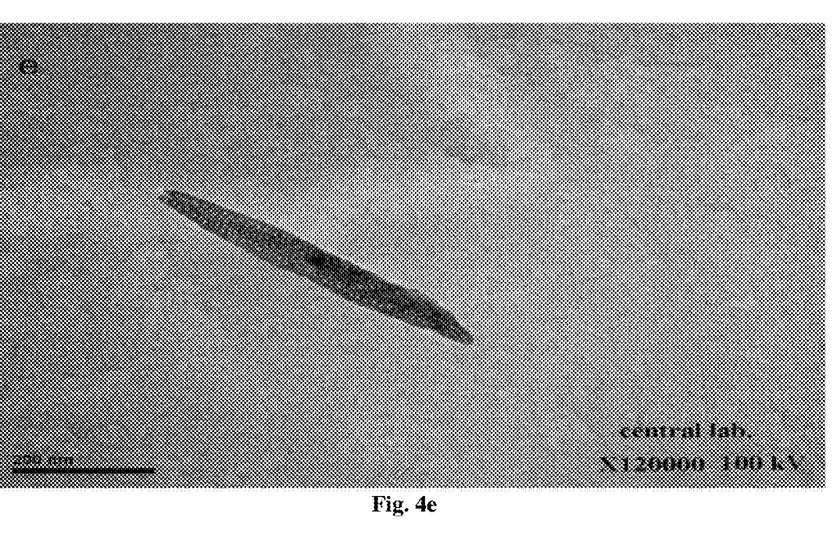
Figure 4F:
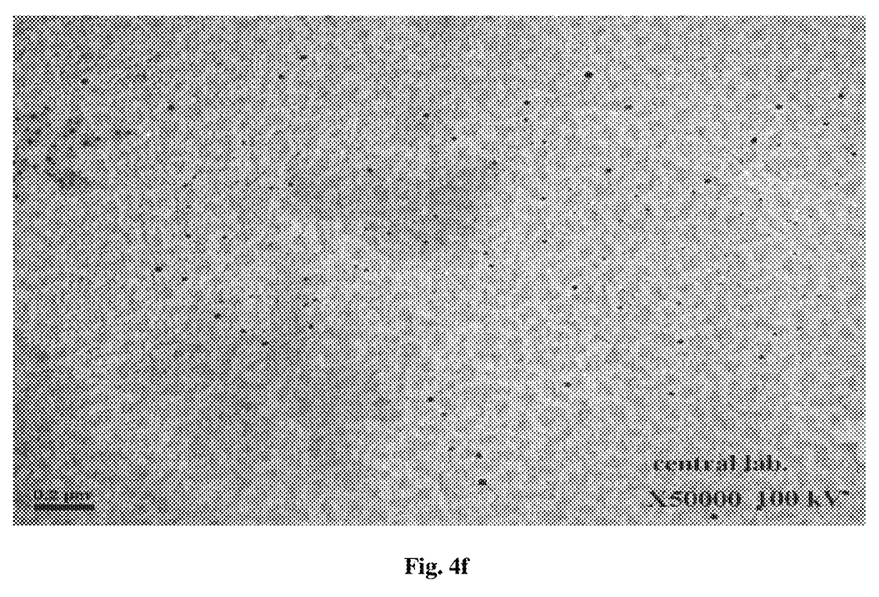
Figure 5A:
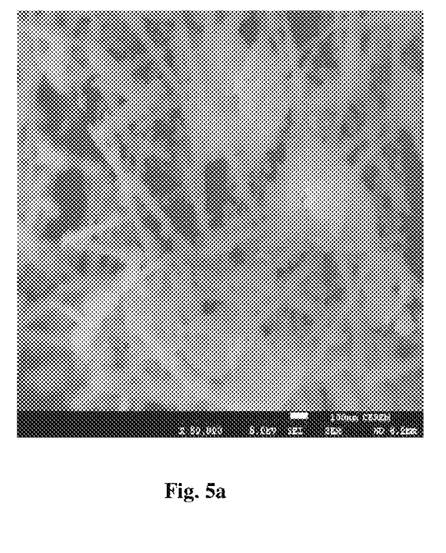
FIGS. 5a, 5b, 5c and 5d show scanning electron microscopy (SEM) images of porous gold oxide nanoparticles.
Figure 5B:
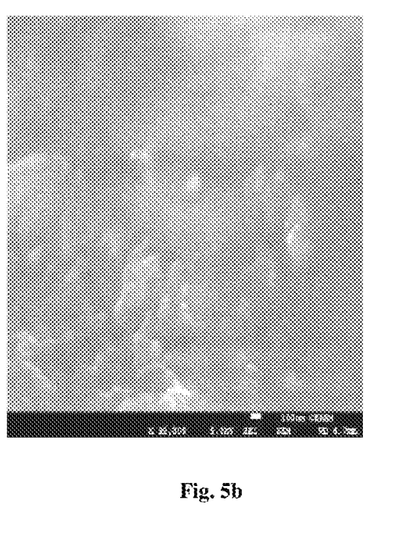
Figure 5C:
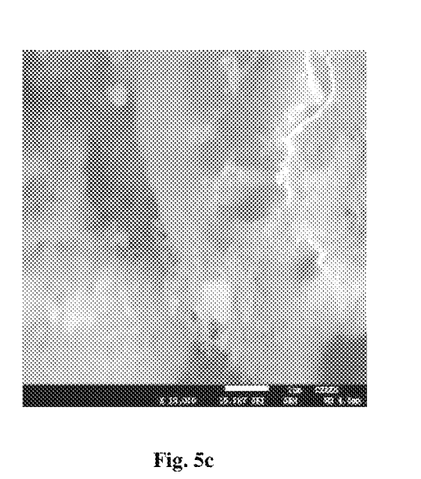
Figure 5D:
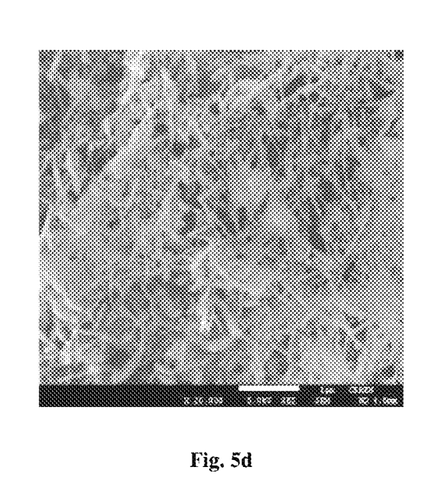
Figure 6:
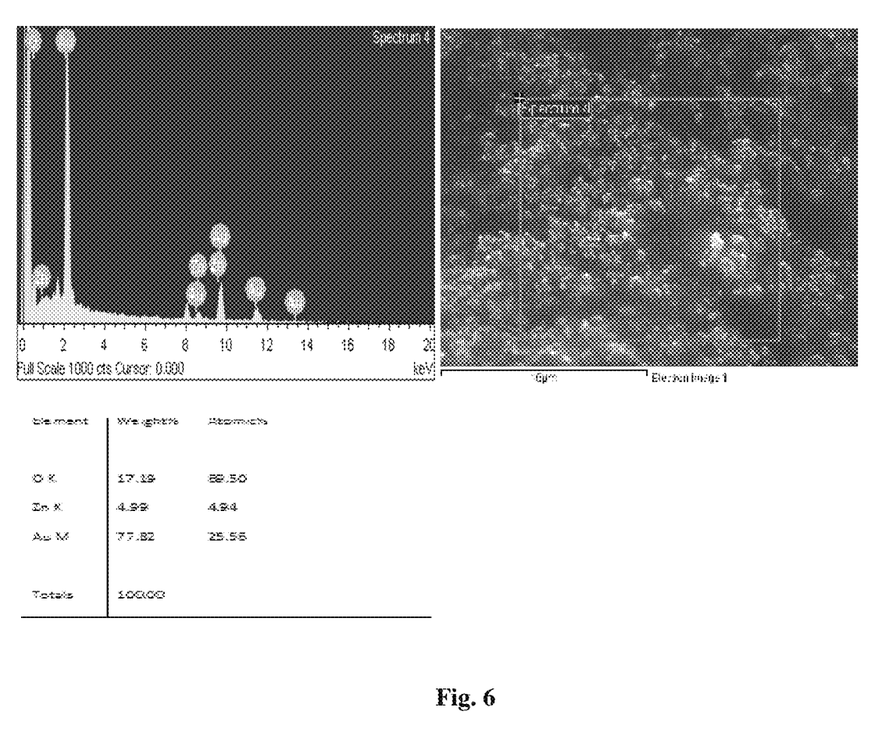
FIG. 6 shows the graph of scanning electron microscopy (SEM) image and elemental analysis by energy-dispersive spectroscopy (EDS) of the inventive porous gold oxide nanoparticles.

The formed porous gold oxide nanoparticles have been analyzed: FIG. 1 shows the absorption peak (SPR) obtained in a visible range at 577.06 nm by UV-visible spectral analysis. This indicates monodispersed porous gold oxide nanoparticles. FIG. 2 shows a graph of Zeta sizer for measuring average size of nanoparticles and the electrical conductivity. The average particles size distribution of porous gold oxide nanoparticles is 36 nm (FIG. 3). Zeta sizer measured high electrical conductivity of 6 mS/cm. Transmission electron microscopy (TEM) images of prepared porous gold oxide nanoparticles are shown in FIGS. 4a to 4f. The porous gold oxide nanoparticles are spherical in shape or smooth rods with a porous surface morphology. EDS spectrum, linked with SEM, was used to analyze the element of the porous gold oxide nanoparticles (FIG. 5).

From Table 1, it can be seen that an increase in calcination temperature leads to an increase in surface area and pore volume of porous gold oxide nanoparticles. The material that has been calcined at 700° C. shows a greater surface area and pore volume in comparison to material calcined at temperatures of 400° C. to 600° C. This increase may be associated with a change in particle size and also removal of impurities and water molecules. Porous gold oxide nanoparticles exhibited smaller pore sizes at 600° C. and 700° C. which might be due to blocking effects of pore networks.

Application of Porous Gold Oxide Nanoparticles

Method of Analysis:

Automated sequential injection (SIA) method for chemiluminescence (CL) determination of tramadol hydrochloride (TR) has been developed. The developed method was based on the enhancement effect of porous gold oxide nanoparticles (AuONPs) on the chemiluminescence (CL) signal arising from luminol-potassium ferricyanide reaction in the presence of tramadol hydrochloride. The optimum conditions relevant to the effect of luminol, potassium ferricyanide and porous AuONPs concentrations were investigated. The proposed method showed linear relationship between the relative CL intensity and the investigated drug concentration at the range of $1.0\times10^{-9}$-$1.0\times10^{-2}$ mol $L^{-1}$, (Correlation coefficient, r=0.9994, number of determinations n=9) with detection limit (N/S=3) of $3.3\times10^{-10}$ mol $L^{-1}$ and quantification limit of $1.0\times10^{-9}$ mol $L^{-1}$. The relative standard deviation was 1.4%. The proposed method was employed for the determination of tramadol hydrochloride in bulk drug and its pharmaceutical dosage forms.

Materials and Reagents:

All reagents were of analytical grade and were used without further purification. Distilled water was used throughout the experiments. Pure grade of tramadol hydrochloride was kindly supplied by Amoun Pharmaceutical Co., Cairo, Egypt. Tramal® ampoules, each ampoule (1 mL) claimed to contain 20 mg tramadol hydrochloride. Chloroauric acid ($HAuCl_4$) was reduced by CTAB extract (mix of Olea Europaea fruit and Acacia Nilotica extracts) and drops of sodium chloride to produce inventive porous AuONPs. Potassium ferricyanide (WINLAB) was used to prepare $1.0\times10^{-2}$ mol $L^{-1}$ solution. Luminol (Sigma Chemical Co.) $1.0\times10^{-4}$ mol $L^{-1}$.

Apparatus:

SIA system (FIAlab-3500 instrument, USA). Fluorimetric/Chemiluminescence UV-detector. Autosampler model ALM 3200. The SIA unit was PC controlled and data acquisition was performed with (FIAlab for windows version 5.9.321) software. The solution stability monitoring and UV spectrophotometry was performed on an UV-Visible Spectrophotometer Ultrospec (model 2100 pro).

Samples Preparation:

Standard Drug Solution:

A stock standard TR solution $1.0\times10^{-1}$ mol $L^{-1}$ was prepared by dissolving 1.499 g of pure drug in 50 mL distilled water. Serial solutions were prepared daily by appropriate dilution. The employed working solutions were in the range of $1.0\times10^{-10}$-$1.0\times10^{-1}$ mol $L^{-1}$.

Preparation of Injection Solutions:

Contents of 10 Tramdol® ampoules (each containing 100 mg/2 mL aqueous tramadol hydrochloride) were mixed. Aliquot solution equivalent to $1.6\times10^{-2}$ was prepared. The working solutions were prepared by serial dilution in the range of $1.0\times10^{-8}$-$1.0\times10^{-3}$ mol $L^{-1}$. The proposed SIA-CL method was employed to determine the investigated drug in each concentration. The mean % recoveries were calculated using calibration graph.

Calibration Curve:

Under the optimum conditions the calibration curve for determination of TR was obtained. The graph related the CL intensity vs. the concentration of tested drug solutions was plotted at 9 experimental points. The mean peak heights were obtained after triplicate sample aspiration. Conventional linear regression was utilized for fitting the curve.

Quantification of tramadol hydrochloride in bulk and ampoules:

The proposed method gave satisfactory results for the determination of TR in pure form. Thus its pharmaceutical dosage form (Tramadol® 100 mg/2 mL) was subjected to the analysis of its TR content by the proposed enhanced AuONPs-SIA CL method. The obtained results are presented in Table 2.

TABLE 2

Performance data obtained from the determination of TR using a AuONPs-luminol/potassium ferricyanide system

| Analytical characteristics | Value |
|---|---|
| Linear range, mol $L^{-1}$ | $1.0\times10^{-9}$-$1.0\times10^{-2}$ |
| Detection limit, mol $L^{-1}$ | $3.3\times10^{-10}$ |
| Quantification limit, mol $L^{-1}$ | $1.0\times10^{-9}$ |
| Intercept on the ordinate | 3578.03 |
| Slope | 45.06 |
| % RSD (n = 9) | 0.4% |
| Correlation coefficient, r | 0.9994 |

TABLE 3

Determination of TR using AuO/NPs-luminol-potassium ferricyanide SIA-injection CL detection in pure form and dosage forms.

| Sample | Taken -log conc. mol $L^{-1}$ | Found | % Recovery | Comparative Example | t-test | F-test | % RSD |
|---|---|---|---|---|---|---|---|
| Pure form | 9.0 | 8.99 | 99.9 | | | | |
| | 8.3 | 8.26 | 99.5 | | | | |
| | 8.0 | 7.98 | 99.8 | | | | |
| | 7.0 | 6.99 | 99.8 | | | | |
| | 6.0 | 5.97 | 99.5 | 99.8 ± 0.6 | 1.67 (2.228)* | 2.50 (5.05)* | 0.4 |
| | 5.0 | 4.95 | 99.0 | | | | |
| | 4.0 | 3.95 | 98.8 | | | | |

TABLE 3-continued

Determination of TR using AuO/NPs-luminol-potassium ferricyanide SIA-injection CL detection in pure form and dosage forms.

| Sample | Taken −log conc. mol $L^{-1}$ | Found | % Recovery | Comparative Example | t-test | F-test | % RSD |
|---|---|---|---|---|---|---|---|
|  | 3.0 | 2.98 | 99.3 |  |  |  |  |
|  | 2.0 | 1.98 | 99.0 |  |  |  |  |
| Mean % ± SD |  | 99.4 ± 0.4 |  |  |  |  |  |
| n |  | 9 |  | 6 |  |  |  |
| Variance |  | 0.16 |  | 0.4 |  |  |  |
| % SE |  | 0.13 |  | 0.2 |  |  |  |
| Tramadol ® 100 mg/ | 8.0 | 7.99 | 99.9 |  |  |  |  |
| 2 mL | 7.0 | 6.96 | 99.4 |  |  |  |  |
|  | 6.0 | 5.97 | 99.5 |  |  |  |  |
|  | 5.0 | 4.93 | 98.6 |  |  |  |  |
|  | 4.0 | 3.94 | 98.5 |  |  |  |  |
|  | 3.0 | 2.95 | 98.3 |  |  |  |  |
| Mean % ± SD |  | 99.0 ± 0.7 |  |  |  |  |  |
| n |  | 6 |  |  |  |  |  |
| Variance |  | 0.49 |  |  | 2.21 (2.228)* | 1.25 (5.05)* | 0.7 |
| % SE |  | 0.29 |  |  |  |  |  |

H. E. Abdelates et al., *J. Pharm. Biometh. Anal.*, 29, 835-842 (2002) reported about kinetic spectrophotometric determination of tramadol hydrochloride in pharmaceutical formulations. Comparative results of this study are also provided in Table 3 (see Comparative Example).

The features disclosed in the foregoing description, claims and the drawings may, both separately or in combination, be material for realizing the invention in diverse forms thereof.

The invention claimed is:

1. Method for preparing porous noble metal oxide nanoparticles, comprising the following steps:
    a) preparing an *Olea Europaea* fruit extract
    b) preparing an *Acacia Nilotica* extract
    c) mixing the *Olea Europaea* fruit extract and the *Acacia Nilotica* extract for preparing a mixed extract
    d) providing an aqueous solution containing a noble metal compound dissolved therein, and
    e) mixing the mixed extract obtained in step c) and the aqueous solution of step d)
    f) dropping a solution of sodium chloride to the mixture of step e)
    g) drying the mixture, and
    h) calcining at a temperature between 100 to 900° C., to get the porous noble metal oxide nanoparticles.

2. Method according to claim 1, wherein the mixed extract obtained in step c) contains oleic acids and/or pentacyclic triterpenoids.

3. Method according to claim 1, wherein the porous noble metal oxide nanoparticles are calcined in step h) at a temperature between 300 to 750° C.

4. Method according to claim 1, wherein the preparation of the *Olea Europaea* fruit extract in step a) is performed by adding deionized or distilled water to *Olea Europaea* fruit.

5. Method according to claim 1, wherein the preparation of the *Acacia Nilotica* extract in step b) is performed by adding deionized or distilled water to *Acacia Nilotica*.

6. Method according to claim 1, wherein the *Olea Europaea* fruit extract and the *Acacia Nilotica* extract are mixed in step c) in a range of weight mixing ratios from 5:1 to 1:5.

7. Method according to claim 1, wherein the noble metal compound comprises is Au or Ag.

8. Method according to claim 1, wherein the noble metal compound is chloroauric acid.

9. Method according to claim 1, wherein the aqueous solution provided in step d) also comprises a surfactant.

10. Porous noble metal oxide nanoparticles prepared by the method of claim 1, wherein the average particle size is within a range of 10-100 nm.

11. Porous noble metal oxide nanoparticles according to claim 10, wherein the noble metal oxide nanoparticles are substantially spherical or rods.

12. Porous noble metal oxide nanoparticles according to claim 10, wherein the porous noble metal oxide nanoparticles have a surface area of 0.05-150 $m^2/g$.

13. Porous noble metal oxide nanoparticles according to claim 10, wherein the porous noble metal oxide nanoparticles have a pore volume of 0.0001-0.7 $cm^3/g$.

14. An automated sequential injection method for chemi-luminescence determination of tramadol hydrochloride, comprising addition of the porous noble metal oxide nanoparticles according to claim 10 to a mixture containing tramadol hydrochloride for chemi-luminescence determination.

15. Method according to claim 9, wherein the surfactant is cetyl trimethyl ammonium bromide (CTAB).

16. Method according to claim 1 wherein the step g) is carried out in in air or by vacuum.

* * * * *